US012758223B2

(12) United States Patent
Litschko

(10) Patent No.: US 12,758,223 B2
(45) Date of Patent: Oct. 13, 2026

(54) CATHETER SYSTEM FOR IMPLANTING A MEDICAL IMPLANT TO FORM A MEDICAL BYPASS CONNECTION

(71) Applicant: BIOTRONIK AG, Buelach (CH)

(72) Inventor: Robert Litschko, Rostock (DE)

(73) Assignee: BIOTRONIK AG, Buelach (CH)

( * ) Notice: Subject to any disclaimer, the term of this patent is extended or adjusted under 35 U.S.C. 154(b) by 112 days.

(21) Appl. No.: 18/857,948

(22) PCT Filed: Apr. 19, 2023

(86) PCT No.: PCT/EP2023/060095
§ 371 (c)(1),
(2) Date: Oct. 18, 2024

(87) PCT Pub. No.: WO2023/208676
PCT Pub. Date: Nov. 2, 2023

(65) Prior Publication Data

US 2025/0255608 A1 Aug. 14, 2025

(30) Foreign Application Priority Data

Apr. 29, 2022 (EP) .................................... 22170916

(51) Int. Cl.
*A61B 17/11* (2006.01)
*A61B 17/00* (2006.01)
(Continued)

(52) U.S. Cl.
CPC ........ *A61B 17/11* (2013.01); *A61B 17/00234* (2013.01); *A61F 2/06* (2013.01);
(Continued)

(58) Field of Classification Search
CPC .......... A61B 17/11; A61B 2017/00252; A61B 2017/1107; A61B 2017/1121; A61B 2017/1135; A61B 2017/1139; A61F 2/064
See application file for complete search history.

(56) References Cited

U.S. PATENT DOCUMENTS 5,797,920 A 8/1998 Kim
5,797,933 A 8/1998 Snow et al.
(Continued)

OTHER PUBLICATIONS

International Search Report and Written Opinion from the corresponding International Patent Application No. PCT/EP2023/060095, dated Jul. 5, 2023.

*Primary Examiner* — Martin T Ton
(74) *Attorney, Agent, or Firm* — Greer, Burns & Crain, Ltd.; Steven P. Fallon

(57) ABSTRACT

A catheter includes a medical bypass implant having a first end, a second end, and a body forming a flow lumen. A catheter shaft defines an inner lumen and a distal end. The inner lumen receives the medical implant in a delivery state such that the first end is arranged near to the distal end and the second end is arranged proximally from the first end. The catheter shaft is moved towards a vessel wall to place the first end on the vessel wall. An actuating catheter is received in the inner lumen. A tip thereof is operatively connected to the second end. The actuating catheter moves the second end towards the first end. The tip is configured to penetrate the vessel wall and to move the second end of the medical implant through the vessel wall.

15 Claims, 4 Drawing Sheets

(51) Int. Cl.
*A61F 2/06* (2013.01)
*A61L 27/36* (2006.01)

(52) U.S. Cl.
CPC . *A61L 27/3604* (2013.01); *A61B 2017/00252* (2013.01); *A61B 2017/00305* (2013.01); *A61B 2017/00876* (2013.01); *A61B 2017/1107* (2013.01); *A61B 2017/1139* (2013.01); *A61F 2210/009* (2013.01); *A61F 2220/0016* (2013.01)

(56) References Cited

U.S. PATENT DOCUMENTS

| | | | | |
|---|---|---|---|---|
| 6,036,072 | A | 3/2000 | Bachinski et al. | |
| 6,113,612 | A * | 9/2000 | Swanson | A61F 2/88 623/1.15 |
| 6,475,222 | B1 * | 11/2002 | Berg | A61M 25/10 606/108 |
| 6,802,847 | B1 * | 10/2004 | Carson | A61B 17/0643 606/153 |
| 2003/0083541 | A1 * | 5/2003 | Sullivan | A61F 2/95 600/36 |
| 2004/0030348 | A1 * | 2/2004 | Peterson | A61F 2/88 606/153 |
| 2007/0118157 | A1 * | 5/2007 | Zuidema | A61B 46/30 606/153 |
| 2010/0036401 | A1 * | 2/2010 | Navia | A61F 2/064 606/155 |
| 2015/0032153 | A1 * | 1/2015 | Quadri | A61M 60/861 606/215 |
| 2016/0278780 | A1 * | 9/2016 | Ishii | A61B 17/11 |

* cited by examiner

CATHETER SYSTEM FOR IMPLANTING A MEDICAL IMPLANT TO FORM A MEDICAL BYPASS CONNECTION

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2023/060095, which was filed Apr. 19, 2023, which application claimed priority from EP application 22170916.5, which was filed Apr. 29, 2022.

FIELD OF THE INVENTION

A field of the invention concerns catheters and medical implants delivered by catheters to form a medical bypass connection on a vessel or between a first vessel and a second vessel.

BACKGROUND

A catheter system of this kind comprises a catheter shaft defining an inner lumen and having a distal end. A medical implant in a delivery state is received in the inner lumen such that a first end of the medical implant is received in proximity to the distal end of the catheter shaft and a second end of the medical implant is arranged proximally with respect to the first end.

To provide a therapy for coronary heart disease (in short CHD) it may be required to form a bypass on a coronary artery in order to overcome an obstruction in a coronary artery and to ensure sufficient blood flow through the coronary arteries, in particular in cases in which a therapy by angioplasty is not easily possible. Whereas within an angioplasty procedure a stent is placed within a narrowed portion of a coronary artery to improve the flow of blood within the coronary artery, a bypass on a coronary artery typically is formed by open heart surgery. To form the bypass, typically a healthy blood vessel is taken from another portion of the patient's body, such as the patient's leg, in order to connect an obstructed portion of a coronary artery to e.g. the aorta to allow blood to flow within the coronary artery.

As an open heart surgery is stressful for a patient and requires a rather long time span of recovery, there is a desire to be able to provide a bypass connection on a vessel or between different vessels, e.g. to provide a therapy for coronary heart disease, in a minimally invasive procedure.

There furthermore is a desire to be able to prepare a medical implant for forming a bypass connection prior to the actual procedure such that a harvesting operation for obtaining a healthy blood vessel from another portion of the patient prior to the actual implant procedure is dispensable.

US 2016/0213462 A1 describes systems and methods for performing transcatheter coronary artery bypass grafting procedures involving passing a graft from the aorta to the coronary artery through the pericardial space. For this, poke-out wires, a coring device, and devices for forming anastomoses at the proximal and distal ends of a vascular graft are employed.

SUMMARY OF THE INVENTION

A preferred catheter for implanting a medical implant to form a medical bypass connection on a vessel or between a first vessel and a second vessel includes a medical implant having a first end, a second end, and a body forming a flow lumen. A catheter shaft defines an inner lumen and includes a distal end. The inner lumen is configured to receive the medical implant in a delivery state of the medical implant such that the first end is arranged near to the distal end and the second end is arranged proximally from the first end. The catheter shaft is configured to be moved towards a vessel wall to place the first end on the vessel wall. An actuating catheter is configured to be received in the inner lumen. The actuating catheter includes a tip operatively connected to the second end. The actuating catheter is movable with respect to the catheter shaft to move the second end towards the first end. The tip is configured to penetrate the vessel wall and to move the second end of the medical implant through the vessel wall.

BRIEF DESCRIPTION OF THE DRAWINGS

The invention shall subsequently be described in more detail with reference to the embodiments shown in the figures. Herein.

DETAILED DESCRIPTION OF THE PREFERRED EMBODIMENTS

Figure 1:
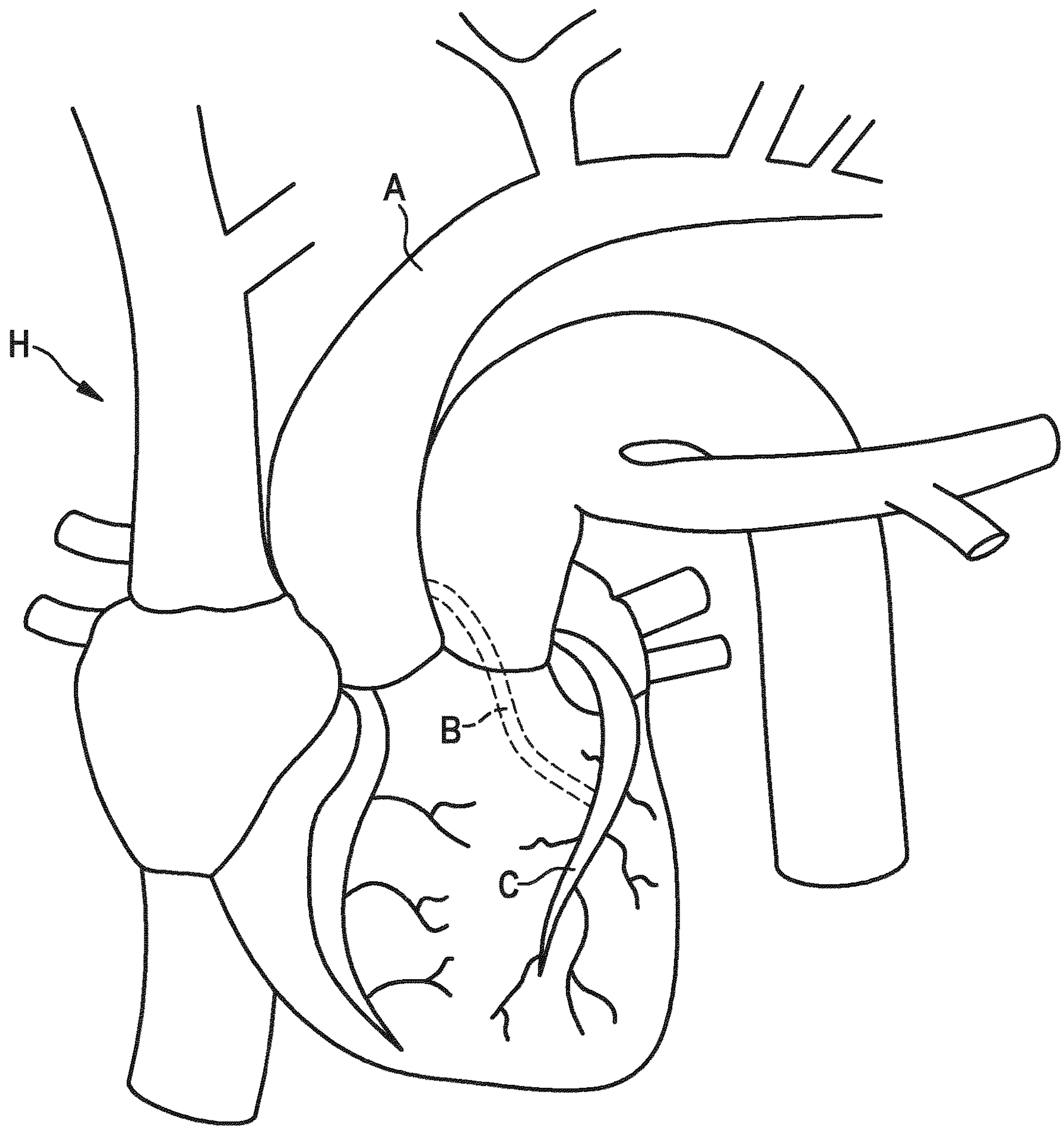
FIG. 1 shows a schematic drawing of the patient's heart.

A preferred catheter system a method for operating a catheter system provide an easy, minimally invasive way to form a medical bypass connection using a medical implant.

In one aspect, a catheter system for implanting a medical implant to form a medical bypass connection on a vessel or between a first vessel and a second vessel includes a medical implant having a first end, a second end and a body forming a flow lumen. The catheter system furthermore includes a catheter shaft defining an inner lumen and having a distal end, the medical implant in a delivery state being received in the inner lumen such that the first end of the medical implant is received in proximity to the distal end of the catheter shaft and the second end is arranged proximally with respect to the first end, wherein the catheter shaft is configured to be moved towards a vessel wall to place the first end of the medical implant on the vessel wall. In addition, the catheter system includes an actuating catheter being received in the inner lumen and having a tip operatively connected to the second end of the medical implant, wherein the actuating catheter is movable with respect to the catheter shaft for approaching the second end of the medical implant towards the first end of the medical implant, the tip being configured to penetrate the vessel wall for moving the second end of the medical implant through the vessel wall.

The catheter system includes a catheter shaft, a medical implant and an actuating catheter. The medical implant, in a delivery state, is received within an inner lumen of the catheter shaft. In addition, the actuating catheter is received in the inner lumen of the catheter shaft. In the delivery state, a first end of the medical implant is placed in proximity to a distal end of the catheter shaft, and the actuating catheter, with a tip, is connected to a second end of the medical implant such that the actuating catheter may act onto the medical implant at the second end.

The catheter shaft, with its distal end, during the implantation procedure is inserted into the patient's body and is moved within the patient's body towards a start location in a vessel, for example within the aortic arc. During the delivery towards the start location the medical implant is received within the catheter shaft, wherein the first end of the medical implant is placed at or in proximity to the distal end of the catheter shaft.

To effect the actual implantation, the catheter shaft with the medical implant received therein is placed with its distal end on a vessel wall, such as the aortic wall in the aortic arc. By placing the distal end of the catheter shaft on the vessel wall, the first end of the implant is arranged on the vessel wall and, during the subsequent placement of the medical implant, remains on the vessel wall.

To form the bypass, now, the actuating catheter is actuated in that the actuating catheter is moved within the inner lumen of the catheter shaft such that the actuating catheter acts onto the medical implant at its second end. The second end in the delivery state is placed proximally with respect to the first end of the medical implant. By actuating the actuating catheter, the second end is caused to approach the first end of the medical implant, and with this the tip of the actuating catheter is approached towards the vessel wall and is caused to penetrate the vessel wall such that the second end of the medical implant is moved through the vessel wall e.g. into the pericardial space beyond the aortic wall.

By guiding the actuating catheter towards a target location and by arranging the second end of the medical implant at the target location, e.g. at a different location of the same vessel or on another vessel, the medical implant with its body is caused to extend between the starting location and the target location such that a medical bypass connection is formed between the starting location and the target location.

The implant procedure may be conducted in a minimally invasive way, e.g. by inserting the catheter system into the patient's artery in the groin to gain vascular access. The implant procedure may be performed while the heart is beating and during regular cardiac activity, hence minimizing the stress on the patient and substantially shortening the recovery time for the patient.

The catheter system may be prepared in advance and may be delivered to a healthcare facility in a prefabricated state. It hence is no longer required to obtain a bypass from a healthy vessel of the patient prior to surgery, but the medical implant may be prefabricated and may be delivered together with the catheter system.

To be able to control the movement of the actuating catheter, the actuating catheter may be implemented by a controllable catheter. In particular, by means of a controllable catheter a target location may be reached by guiding the actuating catheter through a space beyond the vessel wall in a controlled fashion, for example under X-ray guidance and/or by using a sensor on the tip of the actuating catheter.

Instead of using a controllable catheter, a secondary catheter may be inserted into the vessel at the target location, the secondary catheter providing for a marking of the target location.

When implanting the medical implant using the catheter system, the first end of the medical implant is placed on the vessel wall at the starting location and shall remain on the vessel wall when moving the medical implant towards the target location. For this, the medical implant in one embodiment includes a first fixation device arranged at the first end for anchoring the first end to the vessel wall. By means of the first fixation device a fixed connection in between the medical implant and the vessel wall at the first end may be established, such that after placement of the first end of the medical implant on the vessel wall the medical implant with its second end may be moved through the vessel wall and may be approached towards the target location in order to form the bypass connection. Particularly, the fixation device is configured to permanently fix the first end of the medical implant to the vessel wall.

The first fixation device, in one embodiment, includes one or multiple tines being arranged at the first end. The one or the multiple tines may for example be fabricated from a shape-memory alloy, such as a nickel-titanium alloy, particularly nitinol, a nickel-titanium-copper alloy, a copper-zinc alloy, a coper-zinc-aluminum alloy, a copper-aluminum-nickel alloy, an iron-nickel-aluminum alloy, an iron-manganese-silicon alloy or a zinc-gold-copper alloy. When placing the distal end of the catheter shaft on the vessel wall, the first fixation device at the first end of the medical implant is caused to engage with tissue at the vessel wall, the one or the multiple tines e.g. piercing through the vessel wall such that a fixed connection between the medical implant and the vessel wall at the first end of the medical implant is formed.

In one embodiment, the catheter system includes a sheathing which is configured, in the delivery state, to sheathe the first fixation device. By means of the sheathing it is prevented that the first fixation device, for example formed by one or multiple tines, may come into engagement with tissue while moving the catheter system within the patient's vascular system towards the starting location. The sheathing provides for a coverage of the first fixation device during the delivery, wherein by moving the sheathing with respect to the catheter shaft the first fixation device is unsheathed such that the first fixation device may come into engagement with tissue at the starting location.

In a sheathed position the first fixation device for example is held within the sheathing in a deformed position. By moving the sheathing with respect to the catheter shaft the first fixation device is released such that the first fixation device, for example formed by one or multiple tines, may reset to a non-deformed state and, by this, may engage with tissue and may form a fixed connection to the tissue at the starting location on the vessel wall.

The sheathing may in particular be formed by an outer shaft extending outside of the catheter shaft. The sheathing is movable longitudinally along the catheter shaft in order to unsheathe the first fixation device of the medical implant.

In one embodiment, the medical implant includes a sealing device arranged at the first end to establish a sealing between the first end and the vessel wall. The sealing may for example be made from an elastic plastics material and/or may be configured to swell during implantation. By means of the sealing a substantially fluid-tight connection shall be formed between the first end of the medical implant and the vessel wall such that fluid may not exit from the vessel through the through-hole punched into the vessel wall by means of the tip of the actuating catheter during the implantation procedure.

In one embodiment, the medical implant includes a second fixation device arranged at the second end for anchoring the second end to tissue at the target location. By means of the second fixation device the medical implant hence is fixedly connected to the target location beyond an obstruction on the same vessel or on another vessel.

The second fixation device may for example be formed by a magnet element for magnetically interacting with a counter element at the target location. In another embodiment, the second fixation device may include an arrangement of tines or the like. Alternatively, the fixation device may include a helix or screw.

The magnet element and/or the counter element may for example be formed by a ring magnet. The counter element may for example be moved to the target location by using a secondary catheter which also may aide in guiding the actuating catheter towards the target location and to establish a connection of the second end of the medical implant to a vessel portion at the target location.

By moving the actuating catheter through the vessel wall at the starting location and through a space beyond the vessel wall towards a target location, the medical implant is inserted into the space beyond the vessel wall and is guided towards the target location to form a medical bypass connection between the starting location and the target location. In an implanted state, herein, the body of the medical implant in one embodiment extends between the vessel wall at the starting location and the target location on the same vessel or on another vessel to form the medical bypass connection. By means of the body and the flow lumen formed therein a fluid connection is established in between the vessel at the starting location and the vessel at the target location, fluid being able to flow through the body in the implanted state of the medical implant.

In one embodiment, the body is configured to be turned inside out when moving the actuating catheter with respect to the catheter shaft for approaching the second end of the medical implant towards the first end of the medical implant and for moving the second end of the medical implant through the vessel wall. In the delivery state, while moving the catheter system through the vascular system of the patient towards the starting location, the medical implant is received within the inner lumen of the catheter shaft such that the first end of the medical implant is placed at the distal end of the catheter shaft and the second end of the medical implant is received proximally with respect to the first end. The actuating catheter herein is in operative connection to the medical implant at its second end, such that by actuating the actuating catheter the medical implant with its second end is caused to approach the first end. By means of the tip of the actuating catheter the vessel wall is penetrated and by moving the actuating catheter through the vessel wall the medical implant with its second end is likewise moved through the vessel wall while the first end of the medical implant remains on the vessel wall, in particular on a side of the vessel wall facing the inside of the corresponding vessel, for example the aorta. During the actuating movement of the actuating catheter the medical implant is turned inside out, the second end of the medical implant being moved towards the first end and beyond the first end through the vessel wall into the space beyond the vessel wall towards the target location.

By such a movement the implant procedure becomes easy and reliable. Namely, during the implant procedure the first end of the medical implant is fixed to the vessel wall, which can simply be effected by placing the catheter shaft with its distal end on the vessel wall and by unsheathing a fixation device arranged on the first end of the medical implant. Hence, at first the first end of the medical implant is fixed on the vessel wall at the starting location and remains fixed during the further procedure, wherein subsequently to fixing the medical implant at its first end on the vessel wall the second end is caused to approach the target location and in this way the medical implant is turned inside out. By actuating the actuating catheter hence the medical implant with the second end is moved towards the target location and with the second end is fixed at the target location in order to cause the body of the medical implant to extend between the starting location and the target location.

When actuating the actuating catheter, the tip of the actuating catheter is approached towards the distal end of the catheter shaft and is caused to penetrate through the vessel wall at the starting location. To achieve an easy penetration, herein, in one embodiment the actuating catheter includes a cutting edge at the tip for cutting into the vessel wall and to form a through-hole through the vessel wall at the starting location.

In one embodiment, the body of the medical implant is made from a pericardial material. For example, the medical implant may be formed by a tubular member formed from pericardial material. The pericardial material may for example be rolled up to form a tubular member, wherein the pericardial material may be fixated by means of gluing, sewing, or crosslinking to form a tubular structure. Particularly suitable pericardial materials and methods of manufacturing thereof are disclosed in PCT/EP2021/080039, filed Oct. 28, 2021.

In general, all of the above suitable pericardial tissues must be thoroughly cleaned and prepared prior to implantation. As far as possible, the tissue is modified in such a way that it is not recognized by the body as foreign tissue, has as little calcification as possible, and has as long a service life as possible. Essentially, such a method for preparing tissue includes several steps:

One possible preparation step is the so-called decellularization of the tissue. In this step, cell membranes, intracellular proteins, cell nuclei and other cellular components are almost completely removed from the tissue to obtain an approximately pure extracellular matrix. Cells and cellular components remaining in the tissue represent in particular a possible cause of undesired calcification of the biological implant material. Decellularization should be carried out so gently that the structure of the extracellular matrix and in particular the collagen fibers in the extracellular matrix remain as unaffected as possible, while on the other hand all cells and cellular components contained therein are removed from the tissue as completely as possible.

Preferably, the tissue is subjected to a pretreatment, which includes an optional decellularization with a suitable detergent, preferably with a solution containing surfactin and deoxycholic acid. The decellularization can also be performed otherwise, for example, via lysis of the cells or by an osmotic digestion.

After decellularization, as many cellular components as possible are removed from the tissue and the biological material consists exclusively of extracellular matrix. In pericardial tissue, the extracellular matrix is predominantly formed from the collagen fibers. In order to achieve a biological material with the best possible mechanical properties and to prevent defense reactions of the receiving body, in the prior art the collagen fibers are crosslinked by means of a suitable crosslinking agent through the incorporation of chemical bonds.

In one embodiment, the body of the medical implant is made from ultra-thin pericardial tissue. The term “ultrathin tissue” denotes that the treated tissue has a thickness homogeneity characterized by a substantially constant thickness of the tissue of preferably less than 40% of the thickness of the starting tissue (with a tolerance range for a measurement error of ±5 μm) or that the tissue has a thickness of less than 80 μm, preferably between 80 and 20 μm or between 25 μm and 20 μm.

Normally, the normal remaining thickness of a pericardial tissue is 120%-40% of the initial thickness. 120%, i.e. even an increase in thickness, for the case of crosslinking performed freely on a mesh (pericardium becomes thicker during free crosslinking with glutaraldehyde). The thickness reduction is already 40% for standard UTT patches. However, anything below this marks extremely thin patches, where 10% of the initial thickness would be an absolute lower limit. The absolute minimum value for porcine pericardial tissue, for example, is 20 μm thickness.

The above-mentioned adaptation of the tissue properties, such as in particular the thickness, but at the same time also the shape and/or flexibility, is achieved by chemical crosslinking and optional shaping using a permeable material layer (preferably made of a technical fabric), optionally in combination with a (continuous) pressure load on the tissue and the use of an added pressure compensation layer, such as, for example, a compressible foam that is also permeable, or an elastomer mat/silicone mat that is not permeable. Thus, the pressure compensation layer can be permeable, but it does not have to be. Essential for the access of the crosslinking solution to the tissue and for the drainage of the tissue water is the addition of a permeable material layer, e.g. actually only one, or at least two or even more permeable material layers, preferably made of a technical fabric. The at least one, preferably two, permeable material layer(s) may be an organic polymer layer, preferably a polyester layer. The at least one, preferably two, permeable material layer(s) has a mesh size or pore size enabling the crosslinking solution to pass through the permeable material layer(s). This enables a sufficient contact of the tissue with the crosslinking solution passing through the permeable material layer(s). The at least one, preferably two, permeable material layer(s) can have a mesh size or pore size of less than 60 μm, preferably ranging from 10 μm to 60 μm. Mesh sizes or pore sizes of less than 60 μm lead to even tissue surfaces. Mesh sizes or pore sizes larger than 60 μm lead to uneven tissue surfaces so that an imprinted structure on the surface of the biological tissue may be visible to the naked eye. Nevertheless, mesh sizes or pore sizes larger than 60 μm can be used to imprint structures on the surface of the biological tissue if this is desired, namely, whenever one wishes to imprint a technically functional surface on the tissue to be treated, such as, for example, a roughening of a surface or specific depressions in a surface, etc. The at least one, preferably two, permeable material layer can have a thickness of 40 μm to 70 μm. Preferably the tissue is sandwiched between two permeable material layer(s).

Further details of properties and methods of manufacturing of the ultra-thin tissue can be found in PCT/EP2021/080039, particularly on 28, line 1, to 32 line 9.

In one embodiment, the body of the medical implant is made from pericardial tissue shaped by using at least one, in particular a single, rigid molded body in combination with a suitable crosslinking agent, such as glutaraldehyde, and a granulate. The rigid molded body serves as a mere support surface and, if necessary, for shaping the tissue/tissue component, whereas the granulate mechanically fixes the tissue to be shaped to the molded body during the chemical crosslinking process and, at the same time, can be penetrated by the crosslinking solution, such as glutaraldehyde. Further details of properties and methods of manufacturing can be particularly found in PCT/EP2021/080039, particularly on page 68, line 20 to page 73, line 25.

In one embodiment, the body of the medical implant is made by seamlessly connecting pericardial tissue. It is essential for such process that the starting tissue is introduced into the processes substantially non-crosslinked at least in the overlap region (i.e. the tissue region(s) to be joined/connected, but preferably in its entirety; i.e. that, if possible, no substantial pre-crosslinking has taken place, for example by means of glutaraldehyde solution. Substantially non-crosslinked tissue throughout the application means that the proportion of crosslinkable groups in the tissue to be treated (compared to non-crosslinkable groups) is greater than 50%, preferably greater than 60%, even more preferably greater than 80%, most preferably greater than 90%. However, this also means that lightly or only slightly pre-crosslinked or partially crosslinked tissue is suitable for the methods of the first aspect of the invention. However, this also means that lightly or only slightly pre-crosslinked or partially crosslinked tissue is suitable for the processes.

The process particularly involves a chemical crosslinking of tissue joining partners including crosslinkable groups, such as free amino groups, by means of a suitable crosslinking agent under static, quasi-static and periodic pulsatile pressure loading, respectively, in a defined overlap region for seamless, dense and firm material closure. As a result, a seamless, homogeneous, and at the same time mechanically stable connection/joining of tissue/tissue components is achieved. Further details of the process stated above can be particularly found in PCT/EP2021/080039, particularly on page 129, line 11 to page 132, line 14. Advantageously, the therein described tissue may be seamlessly be joined in order to form the body of the medical device by crosslinking, e.g. with glutaraldehyde or the like.

In one embodiment, the body of the medical implant is made of stabilized dry pericardial tissue, involving particularly treating the tissue with a hygroscopic exchange material and a subsequent controlled drying.

In order to enable structure-preserving drying of the tissue, i.e. preservation/stabilization, a hygroscopic exchange material (e.g. glycerol and/or polyethylene glycol, if necessary as mixture(s)) is/are used, which stabilizes the collagen structure when water is removed. In this way, rehydration makes it possible to restore the tissue to its initial state.

Further details of the process of manufacturing stabilized dry pericardial tissue can be found in PCT/EP2021/080039, particularly on page 171, line 28 to page 172, line 23, and on page 178 line 1 to 180.

Fixation devices, such as tines or a magnet element, may be fixed to the body of the medical implant at the first end and at the second end by means of sewing, gluing or by a press-fit connection.

The medical implant may be coated with a medicational substance, for example to counteract a thrombosis risk.

The medical implant may include a reinforcing structure, such as a stent-like wire structure, for example made from a nickel-titanium alloy material such as nitinol, or made from an electro-woven plastics fabric.

The catheter system may be employable for providing for a bypass connection to establish blood flow through a coronary artery. Just as well, the catheter system may be applicable to establish a bypass connection between vessels in another body region, for example in the region of the urinary tract.

In another aspect, a method for operating a catheter system for implanting a medical implant to form a medical bypass connection on a vessel or between a first vessel and a second vessel includes: providing a medical implant having a first end, a second end, a body forming a flow lumen; providing a catheter shaft defining an inner lumen and having a distal end, the medical implant in an initial state being received in the inner lumen such that the first end of the medical implant is received in proximity to the distal end of the catheter shaft and the second end is arranged proximally with respect to the first end; moving the catheter shaft towards a vessel wall to place the first end of the medical implant on the vessel wall; and moving an actuating catheter, which includes a tip operatively connected to the second end of the medical implant, with respect to the catheter shaft, wherein by moving the actuating catheter the second end of the medical implant is approached towards the first end of the medical implant, the vessel wall is penetrated by the tip and the second end of the medical implant is moved through the vessel wall.

The advantages and advantageous embodiments as described above for the catheter system equally apply also to the method, such that it shall be referred to the above explanations in this respect.

In particular, in one embodiment, within the method the body of the medical implant is turned inside out when moving the actuating catheter with respect to the catheter shaft for approaching the second end of the medical implant towards the first end of the medical implant and for moving the second end of the medical implant through the vessel wall. While actuating the actuating catheter to approach the medical implant with the second end towards the target location, the first end remains on the vessel wall at the starting location, such that in an implanted state the body of the medical implant extends between the starting location and the target location and hence establishes a flow connection between the starting location and the target location.

Subsequently, embodiments of the invention shall be described in detail with reference to the drawings. In the drawings, like reference numerals designate like structural elements.

It is to be noted that the embodiments are not limiting for the invention, but merely represent illustrative examples.

Referring to FIG. 1, in coronary heart disease (CHD) an obstruction in a coronary artery C of the patient's heart H may exist which hinders an adequate blood flow through the coronary system of the patient's heart H.

In order to overcome an obstruction in the context of a coronary heart disease, it may be desirous to establish a bypass connection B e.g. between a starting location (prior to the obstruction) and a target location (beyond the obstruction) on a coronary artery C or between e.g. the aorta A in the range of the aortic arc and an obstructed coronary artery C such that blood may flow between the aorta and the coronary artery C.

Whereas typically today a bypass B is implanted in an open heart surgery procedure by taking a portion of a healthy blood vessel e.g. from the patient's leg and by implanting the healthy vessel to form the bypass B, it is desirous to be able to form a bypass connection B between different vessels or on a single vessel to bridge an obstruction by means of a minimally invasive procedure, hence avoiding excessive stress and lengthy recovery times due to the open heart surgery.

Figure 2:
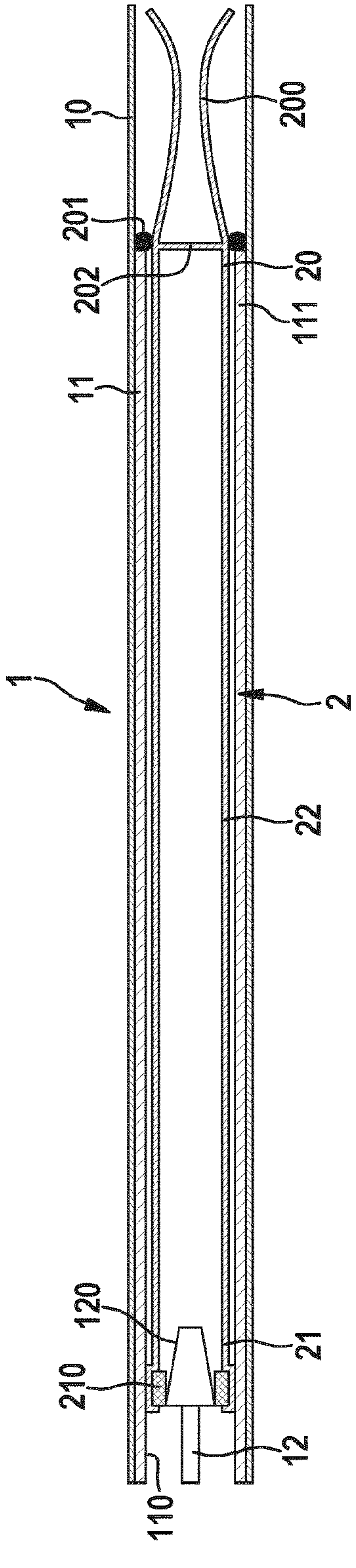
FIG. 2 shows a schematic drawing of an embodiment of a catheter system for establishing a bypass connection.

In order to implant a medical implant 2 to form a bypass connection between a starting location and a target location on an obstructed vessel or between different vessels to overcome an obstruction, it herein is proposed to use a catheter system 1, as shown in an embodiment in FIG. 2, which may be pre-fabricated and delivered to a healthcare facility with a ready-to-implant medical implant 2 received within the catheter system 1.

In the embodiment of FIG. 2, the catheter system 1 includes a catheter shaft 11 forming an inner lumen 110 in which, in a delivery state, the medical implant 2 is received. The medical implant 2 herein, with a first end 20, is placed in proximity to a distal end 111 of the catheter shaft 11, a second end 21 of the medical implant 2 in the delivery state being placed proximally with respect to the first end 20.

At the first end 20 of the medical implant 2, a fixation device 200 is arranged together with a sealing device 201. In the delivery state the fixation device 200—implemented by an arrangement of flexible tines fabricated from a shape memory alloy, preferably a nickel titanium alloy such as nitinol—is received within a sheathing 10 arranged outside of the catheter shaft 11 and circumferentially extending about the catheter shaft 11.

The sheathing 10 in the delivery state holds the fixation device 200 in a deformed state such that tines of the fixation device 200 point forward. The sheathing 10 is slidably movable with respect to the catheter shaft 11 such that, by retracting the sheathing 10 in a proximal direction, the fixation device 200 may be unsheathed, causing the tines of the fixation device 200 to relax towards a non-deformed state in order to provide for a fixation of the medical implant 2 on tissue at a desired location.

The catheter system 1 furthermore includes an actuating catheter 12 which, at a tip 120, is in operative connection with the second end 21 of the medical implant 2. By actuating the actuating catheter 12 the medical implant 2 may be moved in order to establish the bypass connection between a starting location and a target location.

The medical implant 2 includes a body 22 having a tubular shape and defining a flow lumen therein for establishing the bypass connection in between the starting location and the target location.

The medical implant 2 may for example be made from a pericardial material, wherein the pericardial material may for example be rolled up and may be fixated by gluing or sewing to assume a tubular shape defining (in an implanted state, see FIGS. 3A and 4) a flow lumen 220 therein. The fixation device 200 may for example be fixed to the first end 20 of the medical implant 2 by gluing, sewing or by a press-fit connection. Likewise, the sealing device 201 may be fixed to the first end 20 of the medical implant 2 by gluing, sewing or by a press-fit connection.

The connection of the actuating catheter 12 to the second end 21 of the medical implant 2 is releasable, the actuating catheter 12 in particular serving to push the second end 21 of the medical implant 2 forward in a distal direction, as shall subsequently be described in more detail with reference to the sequence of FIGS. 3A to 3E.

The medical implant 2, at the first end 20, may be closed by a septum of 202, which in the course of the implant procedure is pierced by the tip 120 of the actuating catheter 12 such that a flowpath through the medical implant 2 is opened.

Figure 3A:
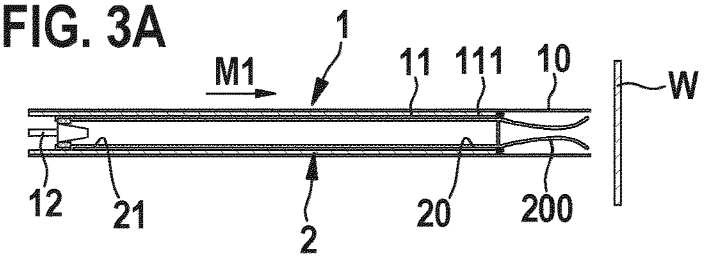
FIG. 3A shows the catheter system in a delivery state.

Referring now to FIG. 3A, the catheter system 1, which may be prefabricated and delivered to a healthcare facility in a ready-to-use state, is inserted into the patient's body e.g. at the femoral artery to obtain a vascular access. The catheter system 1, in the state as shown in FIG. 3A, is advanced towards a starting location for forming the bypass connection, for example at the aortic arc of the patient's heart H to establish a flow connection between the aorta A and a coronary artery C, as illustrated schematically in FIG. 1.

Figure 3B:
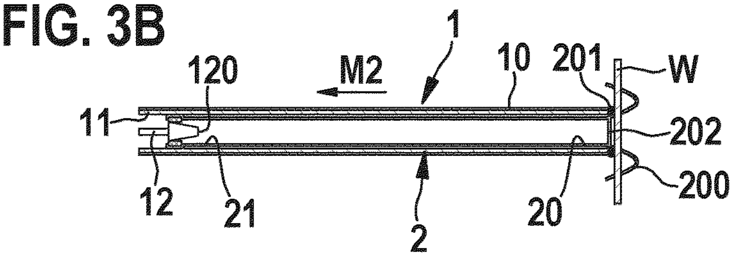
FIG. 3B shows the catheter system when placing a distal end of a catheter shaft on a vessel wall.

At the start of the actual implant procedure, the catheter system 1 is approached towards a vessel wall W, for example the wall of the aorta A at the aortic arc, in a direction of movement M1. As visible from the transition of FIG. 3A to FIG. 3B, by retracting the sheathing 10 in a direction M2 opposite to the direction M1 with respect to the catheter shaft 11, the fixation device 200 at the first end 20 of the medical implant 2 is unsheathed and is caused to engage with the vessel wall W, such that the medical implant 2 at its first end 20 is anchored on the vessel wall W, as shown in FIG. 3B. Particularly, the fixation device 200 is configured to permanently anchor the medical implant 2 at its first end 20 on the vessel wall W.

As visible from FIG. 3A, in the delivery state tines of the fixation device 200 are kept in a deformed state within the sheathing 10. By retracting the sheathing 10 in the direction M2, the tines are caused to relax towards a relaxed, non-deformed state. In that the tines of the fixation device 200 arc outwards and with their free ends point proximally (in the direction M2), the tines by engaging with the vessel wall W cause a tensioning of the medical implant 2 towards the vessel wall W and pull the first end 20 of the medical implant 2 into tight abutment with the vessel wall W.

By placing the medical implant 2 with its first end 20 on the vessel wall W, also the sealing device 201 comes to rest on the vessel wall W in order to provide for a sealing in between the medical implant 2 and the vessel wall W at the first end 20.

Figure 3C:
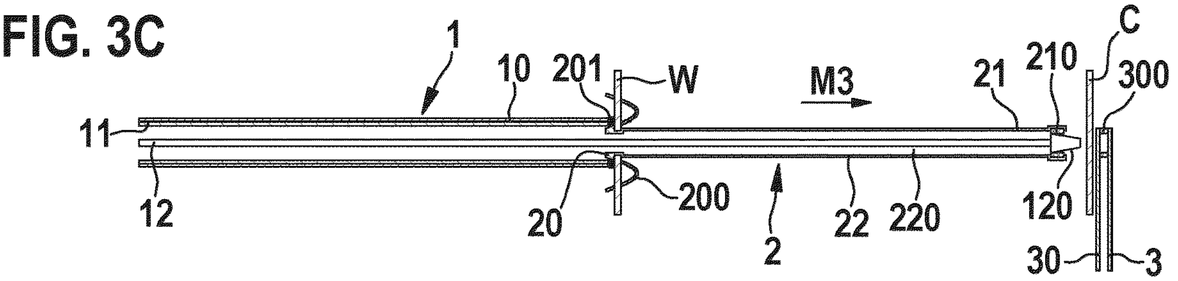
FIG. 3C shows the catheter system while moving an actuating catheter towards a target location.

Subsequent to placing the medical implant 2 with its first end 20 on the vessel wall W, the actuating catheter and 12 is actuated in that the actuating catheter 12 is moved in a direction M3 towards the vessel wall W to pierce through and penetrate the vessel wall W, as shown in the transition of FIG. 3B to FIG. 3C. The actuating catheter 12, for this, includes a cutting edge at its tip 120 such that the tip 120 may easily cut a through-hole into the vessel wall W. Because the actuating catheter 12 at its tip 120 is operatively connected to the medical implant 2 at the second end 21, the second end 21 of the medical implant 2 is carried along when moving the actuating catheter 12 in the direction M3, such that the second end 21 of the medical implant 2 is approached towards the first end 20 and is moved through the vessel wall W into a space beyond the vessel wall W, as visible from the transition between FIG. 3B and FIG. 3C.

During the movement of the actuating catheter 12, the medical implant 2 with its body 22 is turned inside out. Namely, the first end 20 of the medical implant 2 remains on the vessel wall W due to the fixation of the fixation device 200. The second end 21 is moved through the first end 20 and through the vessel wall W and is guided by the actuating catheter 12 towards a target location on another vessel or on a different location of the same vessel, as visible in FIG. 3C.

During the movement of the actuating catheter 12, also a septum 202, if present at the first end 20 of the medical implant 2, is pierced, as visible from the transition of FIG. 3B to FIG. 3C.

The actuating catheter 12 may be a controllable catheter which, for example by using a sensor, may be controlled to approach the target location. In another embodiment, as shown in FIG. 3C a secondary catheter 3 may be inserted into the corresponding vessel at the target location in order to aide a guidance of the actuating catheter 12 towards the target location.

Figure 3D:
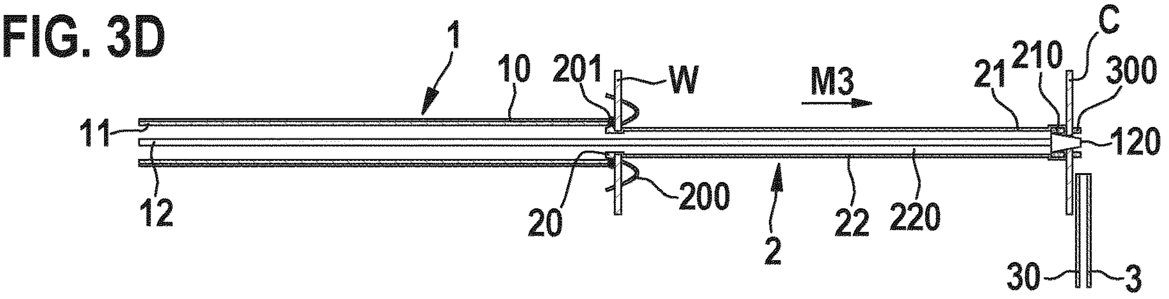
FIG. 3D shows the catheter system after reaching the target location and after fixing the medical implant at the target location.
Figure 3E:
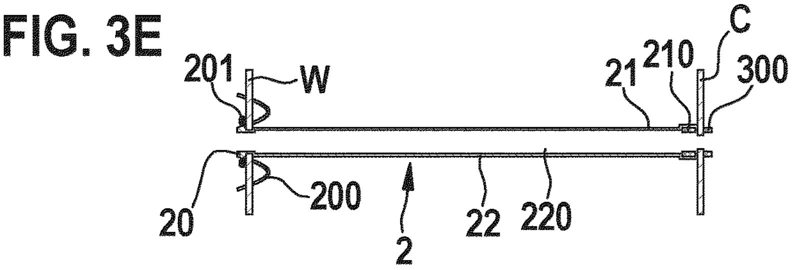
FIG. 3E shows the medical implant in an implanted state.

The secondary catheter 3 for example may carry a counter element 300 formed by a ring magnet to interact with a fixation device 210 arranged at the second end 21 of the medical implant 2 for providing for a fixation of the medical implant 2 to the vessel wall of the corresponding vessel at the target location, as shown in FIG. 3D.

In particular, the fixation device 210 formed by a ring magnet arranged on the second end 21 of the medical implant 2 may magnetically interact with the counter element 300 such that the vessel wall at the target location is clamped in between the magnet element 210 and the counter element 300. By advancing the actuating catheter 12 further, the vessel wall at the target location is penetrated and a through-hole is established at the target location such that a flowpath through the body 22 of the medical implant 2 is opened and a fluid connection in between the starting location at the vessel wall W and the target location is established.

When now removing the catheter shaft 11 together with the actuating catheter 12 and the sheathing 10, the medical implant 2 remains in place and forms a bypass connection between the starting location and the target location on an obstructed vessel or between two different vessels.

Figure 4:
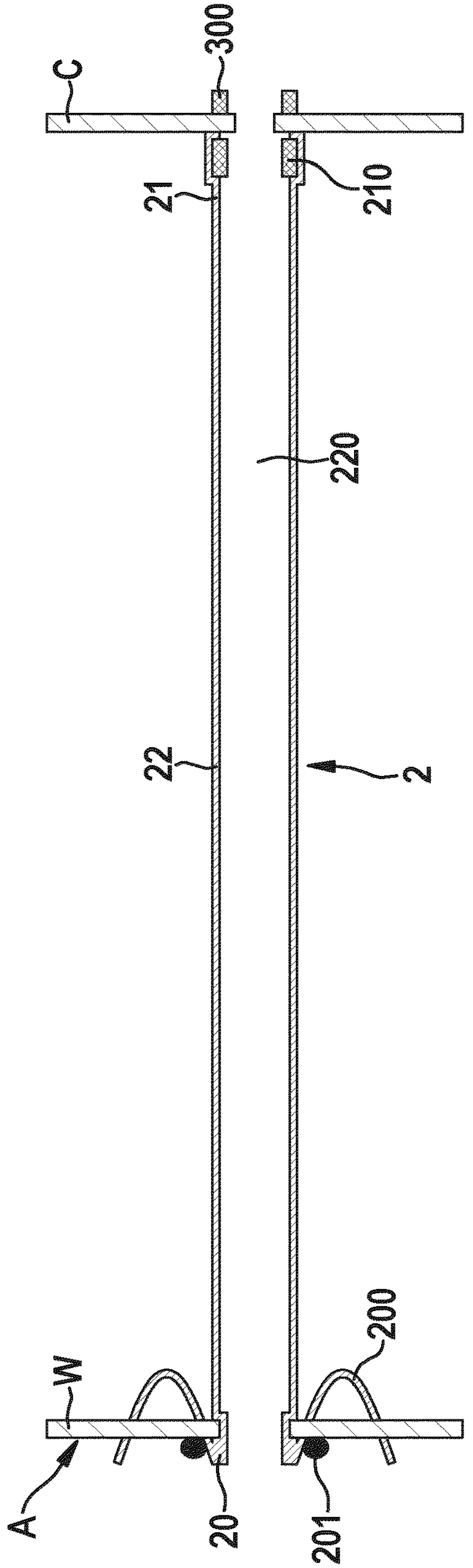
FIG. 4 shows an enlarged view of the drawing of FIG. 3E.

FIG. 4 shows the arrangement of FIG. 3B in an enlarged view. In the implanted state the medical implant 2 at its first end 20 is fixed to the vessel wall W for example at the aorta A e.g. in the range of the aortic arc of the patient's heart H. The first end 20 herein rests at an inner side of the aortic vessel wall W. At the second end 21 the medical implant 2 is fixed to the target location, e.g. of the coronary artery C. Whereas a fixation at the starting location is provided by tines of a first fixation device 200 at the first end 20 of the medical implant 2, a fixation at the second end 21 is established by a magnet element of the fixation device 210 interacting with a counter element 300 to establish a clamping connection at the target location C.

Sealing devices 201 may be placed at either end 20, 21 of the medical implant 2. A sealing device 201 in particular serves to establish a sealed connection during the implantation procedure and during subsequent operation in order to avoid a leakage of blood through the vessel walls into a pericardial space.

The idea underlying the invention is not limited to the embodiments described above, but may be implemented in an entirely different fashion.

A bypass connection may be established, by using the catheter system, in between the aortic arc and a coronary artery or in between different locations of an obstructed coronary artery. Just as well, the catheter system may be used to establish a bypass connection for example in the urinary tract of the patient or in another body region.

The turning inside out of the medical implant during the implantation procedure may be forced by the actuating catheter, wherein the movement of the medical implant may be supported for example hydraulically by causing e.g. a saline solution flow within the catheter system.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

LIST OF REFERENCE NUMERALS

1 Catheter system
10 Sheathing
11 Catheter shaft

110 Inner lumen
111 Distal end
12 Actuating catheter
120 Tip
2 Implant device
20 First end
200 Fixation device
201 Sealing device
202 Septum
21 Second end
210 Fixation device
22 Body
220 Flow lumen
3 Secondary catheter
30 End
300 Counter element
A Aortic arch
B Bypass
C Coronary artery
H Heart
M1-M3 Direction of movement
W Vessel wall

The invention claimed is:

1. A catheter for implanting a medical implant to form a medical bypass connection on a vessel or between a first vessel and a second vessel, comprising:

a medical implant comprising a first end, a second end, and a body forming a flow lumen;

a catheter shaft defining an inner lumen and comprising a distal end, wherein said inner lumen is configured to receive the medical implant in a delivery state of the medical implant such that the first end is arranged near to said distal end and the second end is arranged proximally from the first end, wherein the catheter shaft is configured to be moved towards a vessel wall to place the first end on the vessel wall; and an actuating catheter configured to be received in said inner lumen, wherein the actuating catheter comprises a tip operatively connected to the second end, wherein the actuating catheter is movable with respect to the catheter shaft to move the second end towards the first end, wherein said tip is configured to penetrate the vessel wall and to move the second end of the medical implant through the vessel wall, wherein the body is configured to be turned inside out by moving said tip towards and past the first end to move the second end through the vessel wall.

2. The catheter system according to claim 1, wherein the medical implant comprises a first fixation device arranged at the first end configured to anchor said first end to the vessel wall.

3. The catheter system according to claim 2, wherein the first fixation device comprises at least one tine arranged at the first end and configured to engage with tissue of the vessel wall.

4. The catheter system according to claim 2, comprising a sheathing configured, in said delivery state, to sheath said first fixation device, the sheathing being movable with respect to the catheter shaft to unsheathe said first fixation device to engage with tissue of the vessel wall.

5. The catheter system according to claim 2, wherein the medical implant comprises a second fixation device arranged at the second end configured to anchor said second end to tissue at a target location.

6. The catheter system according to claim 5, wherein the second fixation device comprises a magnet arranged to magnetically interact with a counter element at the target location.

7. The catheter system of claim 6, comprising a secondary catheter configured to deliver said counter element to the target location.

8. The catheter system of claim 5, wherein the body is configured to extend between the vessel wall and the target location to form said medical bypass connection in an implanted state of the medical implant.

9. The catheter system according to claim 1, wherein the medical implant comprises a sealing device arranged at said first end, the sealing device being configured to establish a seal between said first end and the vessel wall.

10. The catheter system according to claim 9, wherein the sealing device comprises an elastic plastics material.

11. The catheter system according to claim 9, wherein the sealing device is configured to swell during implantation.

12. The catheter system of claim 1, wherein the tip comprises a cutting edge configured to penetrated the vessel wall.

13. The catheter system of claim 1, wherein the body comprises a pericardial material.

14. A method for operating a catheter system for implanting a medical implant to form a medical bypass connection on a vessel or between a first vessel and a second vessel, said method comprising:

providing a medical implant comprising a first end, a second end, and a body forming a flow lumen;

providing a catheter shaft defining an inner lumen and comprising a distal end, said medical implant being configured in an initial state to be received in said inner lumen such that the first end is near to said distal end and the second end is arranged proximally from the first end;

moving the catheter shaft towards a vessel wall to place the first end on the vessel wall; and moving an actuating catheter, which comprises a tip operatively connected to the second end, with respect to the catheter shaft to move the second end towards and past the first end to penetrate the vessel wall and move the tip and the second end through the vessel wall.

15. The method of claim 14, wherein the moving the actuating catheter turns the body inside out by passing the second end through the first end.

* * * * *